(12) United States Patent
Sindledecker et al.

(10) Patent No.: US 9,255,595 B2
(45) Date of Patent: Feb. 9, 2016

(54) OPTICAL DOME BEZEL

(75) Inventors: Glenn Sindledecker, Dracut, MA (US);
Gerard A. Esposito, Chelmsford, MA
(US); Sixing She, Wilmington, MA (US)

(73) Assignee: **BAE Systems Information and
Electronic Systems Integration Inc.**,
Nashua, NH (US)

( * ) Notice: Subject to any disclaimer, the term of this patent is extended or adjusted under 35 U.S.C. 154(b) by 538 days.

(21) Appl. No.: 13/809,330

(22) PCT Filed: Apr. 16, 2012

(86) PCT No.: PCT/US2012/033756
§ 371 (c)(1),
(2), (4) Date: Jan. 9, 2013

(87) PCT Pub. No.: WO2012/148719
PCT Pub. Date: Nov. 1, 2012

(65) Prior Publication Data
US 2013/0114141 A1 May 9, 2013

Related U.S. Application Data

(60) Provisional application No. 61/481,054, filed on Apr. 29, 2011.

(51) Int. Cl.
*G02B 7/20* (2006.01)
*F16B 17/00* (2006.01)
(Continued)

(52) U.S. Cl.
CPC ........... *F16B 17/00* (2013.01); *A61K 47/48384* (2013.01); *A61K 47/48561* (2013.01);
(Continued)

(58) Field of Classification Search
CPC ............... C07K 16/22; C07K 16/2896; A61K 47/48561; A61K 47/48384; F16B 17/00; G02B 27/0006; G02B 7/28; G02B 23/16; G02B 7/00; G02B 7/02; G02B 7/20
USPC ......................................... 359/507, 511, 513
See application file for complete search history.

(56) References Cited

U.S. PATENT DOCUMENTS 3,624,379 A 11/1971 Bliss et al.
3,878,388 A 4/1975 Germany
(Continued)

FOREIGN PATENT DOCUMENTS

FR 2921408 3/2009
WO WO2009158422 12/2009

*Primary Examiner* — Jennifer L. Doak
(74) *Attorney, Agent, or Firm* — Daniel J. Long; Finch & Maloney PLLC

(57) ABSTRACT

Techniques and architecture are disclosed for implementing an optical dome bezel to interface an optical dome/window and a housing of differing coefficients of thermal expansion (CTEs), In some embodiments, the bezel may comprise a material (e.g., Ti-6Al-4V) that is CTE-matched to the optical dome material (e.g., silicon, germanium, sapphire, ALON), thereby mitigating temperature effects on system performance. In some embodiments, the bezel may include a radially compliant flexure feature (e.g., flexure blades, spring-form S-channels), which mitigates physical stress effects (e.g., vibration, thermal expansion/contraction, etc.) on system performance. In some embodiments, the bezel may include an integral environmental sealing feature (e.g., O-ring gaskets), which protects internal optics/electronics from external environmental hazards (e.g., moisture, corrosive substances, particulates, debris). In some embodiments, the bezel may be efficiently and repeatedly removed/replaced while preserving optical system performance. Numerous configurations and variations will be apparent in light of this disclosure.

25 Claims, 5 Drawing Sheets

(51) Int. Cl.
*C07K 16/22* (2006.01)
*C07K 16/28* (2006.01)
*G02B 27/00* (2006.01)
*A61K 47/48* (2006.01)
*A61K 39/00* (2006.01)

(52) U.S. Cl.
CPC .............. *C07K16/22* (2013.01); *C07K 16/2896* (2013.01); *G02B 27/0006* (2013.01); *A61K 2039/505* (2013.01); *A61K 2300/00* (2013.01); *C07K 2317/24* (2013.01); *C07K 2317/73* (2013.01); *C07K 2317/76* (2013.01); *C07K 2317/92* (2013.01)

(56) References Cited

U.S. PATENT DOCUMENTS

| | | | |
|---|---|---|---|
| 4,405,973 | A | 9/1983 | Moscarillo |
| 5,951,151 | A | 9/1999 | Doubeck et al. |
| 8,899,761 | B2 * | 12/2014 | Tonar et al. .................... 359/511 |
| 2003/0063470 | A1 | 4/2003 | Grajetzky et al. |
| 2006/0104806 | A1 | 5/2006 | Giesler et al. |
| 2007/0252528 | A1 | 11/2007 | Vermuelen et al. |
| 2010/0002422 | A1 | 1/2010 | Ho |
| 2010/0034530 | A1 * | 2/2010 | Son ............................... 396/427 |
| 2013/0208367 | A1 * | 8/2013 | Thomas et al. ............... 359/732 |

* cited by examiner

Figure 5B
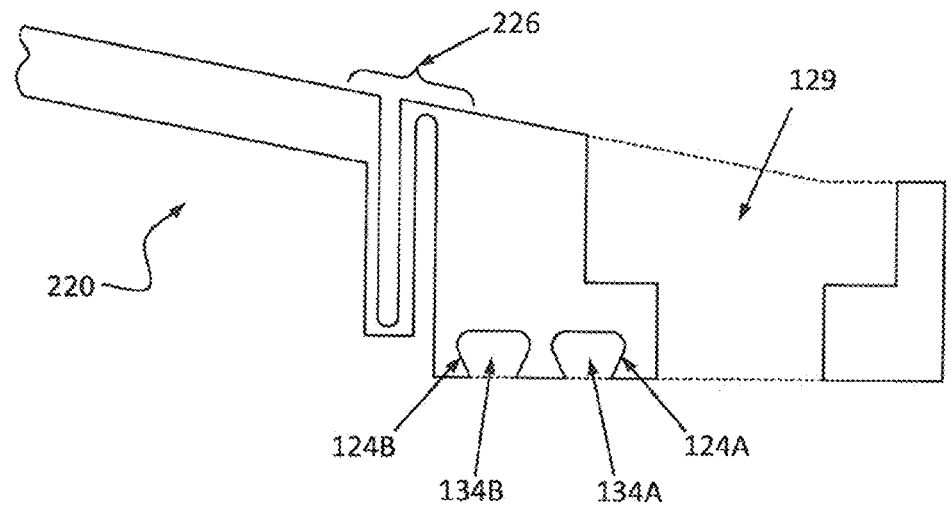
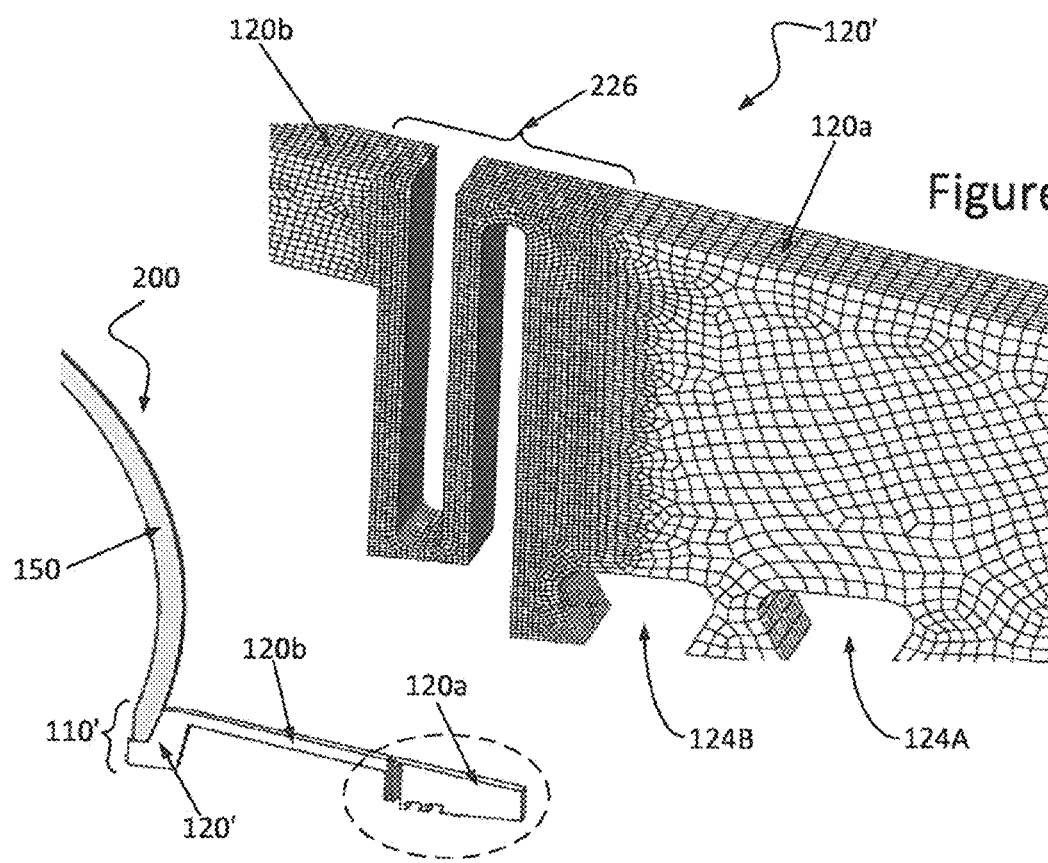
Figure 6A
Figure 6B

OPTICAL DOME BEZEL

CROSS-REFERENCE TO RELATED APPLICATIONS

This application claims the benefit of and priority to U.S. Provisional Patent Application No. 61/481,065, filed on Apr. 29, 2011, which is herein incorporated by reference in its entirety.

FIELD OF THE DISCLOSURE

The invention relates generally to optical housings and more particularly to optical dome interfacing.

BACKGROUND

Optical housing design involves a number of non-trivial challenges, and optical dome interfacing has faced particular complications, such as those with respect to protecting the integrity of internally housed optics/electronics over a broad range of temperatures and other environmental stressors.

SUMMARY

One example embodiment of the present invention provides an apparatus including a mounting ring having an aperture passing therethrough from an exterior surface of the mounting ring to an opposing, interior surface thereof, a radially compliant flexure feature integral wife the mounting ring, and an environmental sealing feature integral with the mounting ring. In some cases, the mounting ring comprises Grade 5 titanium alloy (Ti-6Al-4V), a low-expansion iron-nickel alloy, a low-expansion stainless steel, and/or an aluminum-beryllium composite. In some cases, the aperture is configured to receive a quantity of adhesive sealant for bonding an optical dome/window to the mounting ring. In some cases, the radially compliant flexure feature comprises a plurality of flexure blades disposed along an outer perimeter of the mounting ring and extending substantially perpendicular to the interior surface of the mounting ring. In some such cases, at least one flexure blade further includes a flexure foot located at a distal end of the flexure blade and extending radially outward substantially parallel to the interior surface of the mounting ring and a precision alignment feature located at the distal end of the flexure blade, positioned opposite the flexure foot, and extending radially inward substantially parallel to the interior surface of the mounting ring. In some cases, the radially compliant flexure feature comprises a continuous spring-form S-channel integrally formed in tire mounting ring. In some cases, the environmental sealing feature includes a first channel integral with the interior surface of the mounting ring at a first radial distance and a second channel integral with the interior surface of the mounting ring at a second radial distance of lesser radius than the first channel. In some such cases, at least one of the first, channel and/or the second channel contains a sealing material that is resistant to at least one of water, rain, humidity, moisture, steam, corrosive fluids, corrosive vapors, fuels, lubricants, greases, solvents, ozone, particulates, dust, smoke, and/or debris over a temperature range of about −60° C. to 90° C. In some such eases, the first channel contains a fluorosilicone O-ring gasket, and the second channel contains a butyl O-ring gasket. In some cases, the apparatus includes a protective ring/sleeve configured to be received by the aperture and to protect at least a portion of the mounting ring and/or an optical dome/window received by tire mounting ring during operative coupling of the apparatus with a housing. In some such cases, the protective ring/sleeve comprises the same material as the mounting ring.

Another example embodiment of the present invention provides a system including an optical dome/window and a bezel configured to receive the optical dome/window, wherein the bezel includes a mounting ring having an aperture passing therethrough from an exterior surface of the mounting ring to an opposing, interior surface, thereof, a radially compliant flexure feature integral with the mounting ring, and an environmental sealing feature integral with the mounting ring. In some cases, the optical dome/window comprises at least one of aluminum oxynitride (ALON), silicon, germanium, and/or sapphire. In some cases, the optical dome/window is configured with a geometry selected from the group consisting of spherical, ellipsoidal, polyhedral, cubic, prismatic, cylindrical, planar, curvilinear, and non-planar, in some cases, the mounting ring comprises Grade 5 titanium alloy (Ti-6Al-4V), a low-expansion iron-nickel alloy, a low-expansion stainless steel, and/or an aluminum-beryllium composite. In some cases, the radially compliant flexure feature comprises a plurality of flexure blades positioned along an outer perimeter of the mounting ring and extending substantially perpendicular to the interior surface of the mounting ring. In some such cases, at least one flexure blade further includes a flexure foot located at a distal end of the flexure blade and extending radially outward substantially parallel to the interior surface of the mounting ring and a precision alignment feature located at the distal end of the flexure blade, positioned opposite the flexure foot, and extending radially inward substantially parallel to the interior surface of the mounting ring. In some cases, the radially compliant flexure feature comprises a continuous spring-form S-channel integrally formed in the mounting ring. In some cases, the environmental sealing feature includes a first channel integral with tire interior surface of the mounting ring at a first radial distance and a second channel integral with the interior surface of the mounting ring at a second radial distance of lesser radius than the first channel, wherein at least one of the first channel and/or the second channel contains an O-ring gasket mat is resistant to at least one of water, rain, humidity, moisture, steam, corrosive fluids, corrosive vapors, fuels, lubricants, greases, solvents, ozone, particulates, dust, smoke, and/or debris over a temperature range of about −60° C. to 90° C. In some cases, the bezel further includes a protective ring/sleeve configured to be received by the aperture and to protect at least a portion of the mounting ring and/or optical dome/window during operative coupling of the bezel with a housing. In some cases, the bezel is configured to operatively couple with a housing comprising a material having a different coefficient of thermal expansion from that of the optical dome/window, and wherein the bezel is configured to at least one of provide a substantially stress-free bezel-to-optical dome/window interface over a temperature range of about −60° C. to 90° C. and/or provide a low-stress bezel-to-housing interface over a temperature range of about −60° C. to 90° C. while exhibiting radially compliant flexure.

Another example embodiment of the present invention provides a system including a bezel including an annular mounting ring having an aperture passing therethrough from an exterior surface of the mounting ring to an opposing, interior surface thereof, a plurality of flexure blades positioned along an outer perimeter of the mounting ring, wherein the flexure blades extend substantially perpendicular to the inner surface of the mounting ring, and wherein at least one flexure blade further includes a flexure foot located at a distal end of the flexure blade and extending radially outward substantially parallel to the interior surface of the mounting ring and a precision alignment feature located at the distal end of the flexure blade, positioned opposite the flexure foot, and extending radially inward substantially parallel to the interior surface of the mounting ring, a first channel formed in the interior surface of the mounting ring at a first radial distance, a fluorosilicone O-ring gasket disposed within the first channel, a second channel formed in the interior surface of the mounting ring at a second radial distance of lesser radius than the first channel, and a butyl O-ring gasket disposed within the second channel, an optical dome/window operatively coupled to the bezel at the aperture, and an optical component positioned within the bezel. In some cases, the mounting ring comprises a material having a coefficient of thermal expansion within 20% or less than that of the optical dome/window. In some cases, the bezel further includes a protective ring/sleeve configured to be received by the aperture and to protect at least a portion of the bezel and/or optical dome/window during operative coupling of the bezel with a housing, and wherein the protective ring/sleeve comprises a material having a coefficient of thermal expansion within 20% or less than that of the mounting ring and/or the optical dome/window. In some cases, the bezel is configured to operatively couple with a housing comprising a material having a different coefficient of thermal expansion from that of the optical dome/window, and wherein the bezel is configured to at least one of provide a substantially stress-free bezel-to-optical dome/window interlace over a temperature range of about −60° C. to 90° C. and/or provide a low-stress bezel-to-housing interface over a temperature range of about −60° C. to 90° C. while exhibiting radially compliant flexure.

The features and advantages described herein are not all-inclusive and, in particular, many additional features and advantages will be apparent to one of ordinary skill in the art in view of the drawings, specification, and claims. Moreover, it should be noted that the language used in the specification has been selected principally for readability and instructional purposes and not to limit the scope of the inventive subject matter.

BRIEF DESCRIPTION OF THE DRAWINGS

FIG. 5B illustrates a partial, cross-section view of the optical dome bezel assembly of FIG. 5A, the view corresponding to the portion enclosed by tire dashed ellipse therein.

FIG. 6A illustrates a partial, cross-section view of an optical dome bezel assembly configured in accordance with an embodiment of the present invention.

FIG. 6B illustrates a partial, cross-section view of the optical dome bezel assembly of FIG. 6A, the view corresponding to the portion enclosed by the dashed ellipse therein.

Figure 1:
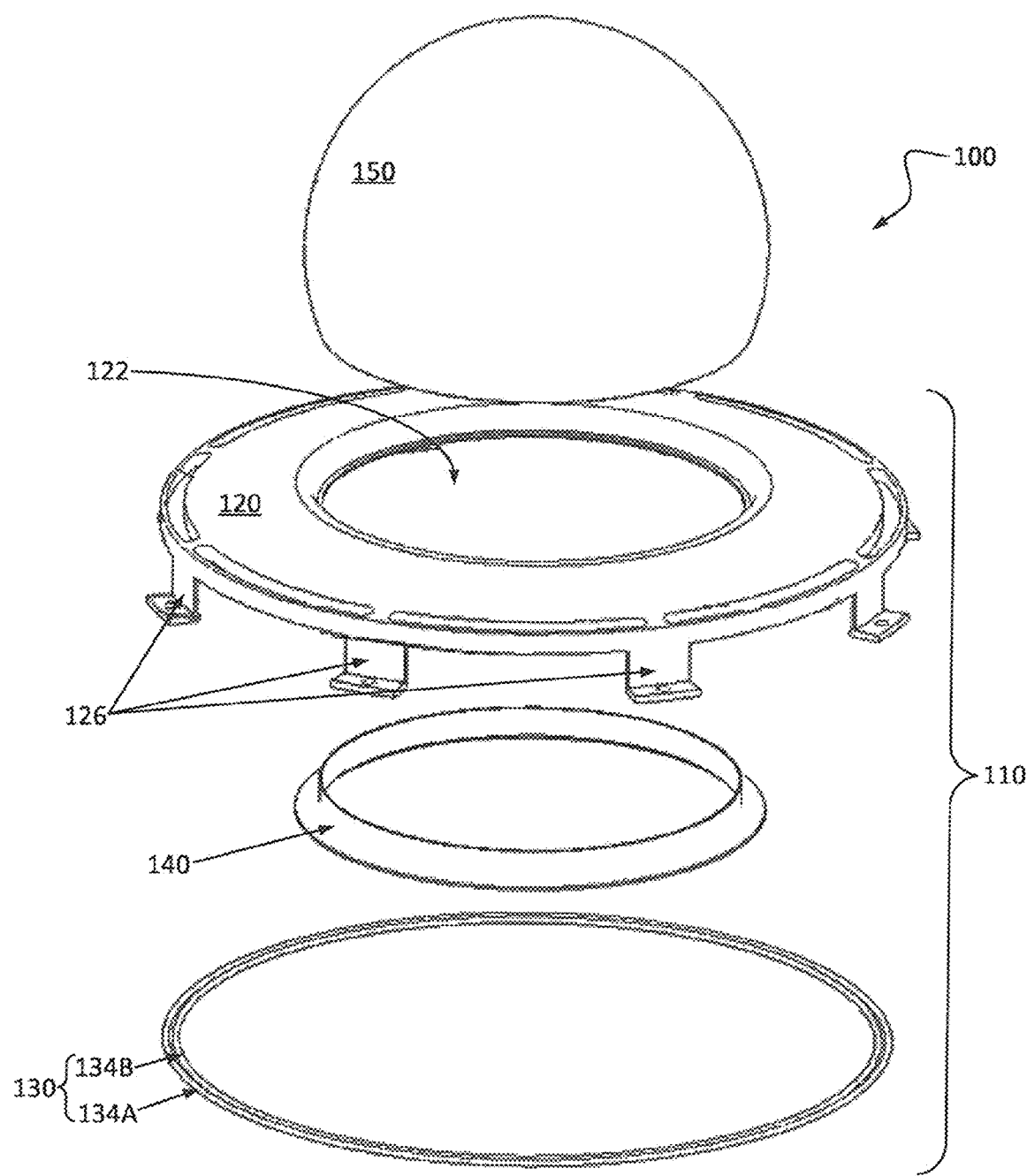
FIG. 1 illustrates an exploded view of an optical dome bezel assembly configured in accordance with an embodiment of the present invention.

These and other features of the present embodiments will be understood better by reading the following detailed description, taken together with the figures herein described. The accompanying drawings are not intended to be drawn to scale. In the drawings, each identical or nearly identical component that is illustrated in various figures is represented by a like numeral. For purposes of clarity, not every component may be labeled in every drawing.

DETAILED DESCRIPTION

Techniques and architecture are disclosed for implementing an optical dome bezel to interface an optical dome/window and a housing of differing coefficients of thermal expansion (CTEs). In some embodiments, the bezel may comprise a material (e.g., Ti-6Al-4V) that is CTE-matched to the optical dome material (e.g., silicon, germanium, sapphire, ALON), thereby mitigating temperature effects on system performance. In some embodiments, the bezel may include a radially compliant flexure feature (e.g., flexure blades, spring-form S-channels), which mitigates physical stress effects (e.g., vibration, thermal expansion/contraction, etc.) on system performance. In some embodiments, the bezel may include an integral environmental sealing feature (e.g., O-ring gaskets), which protects internal optics/electronics from external environmental hazards (e.g., moisture, corrosive substances, particulates, debris). In some embodiments, the bezel may be efficiently and repeatedly removed/replaced while preserving optical system performance. Numerous configurations and variations will be apparent in light of this disclosure.

General Overview

As previously indicated, there are a number of non-trivial issues regarding optical dome interfacing. For instance, one such non-trivial issue pertains to achieving and maintaining an environmental seal which protects the internally housed optics/electronics from external environmental hazards over a broad range of temperatures.

Another non-trivial issue pertains to managing thermal stress loads normally induced by differences in coefficient of thermal expansion (CTE) between the various materials used in optical dome interface designs. As will be appreciated, upon subjecting such a design to repeated heating/cooling, the CTE-mismatched materials in physical contact with (or otherwise sufficiently proximate) one another may suffer physical damage (e.g., loosening of components, breaking of welds, interface cracking, warping, etc.), thereby degrading system performance and reliability. Furthermore, CTE matching optical system components is often prohibitively costly.

Yet another non-trivial issue pertains to maintaining the precision/accuracy of the optics system. As will be appreciated, removal/replacement of interface components typically produces inconsistencies/variations in the positioning/alignment of such components relative to the internal optics. Consequently, significant errors/deviations in the information/data gathered from a scene within the optical system's field of view (FOV) may result.

There exist optical dome bezel systems which provide environmental sealing, but which do not provide radially compliant flexure to accommodate CTE mismatching. Contrariwise, there exist optical mounting systems which provide radially compliant flexure, but which do not include environmental sealing provisions. As such, such designs have not been able to simultaneously accommodate, for example, environmental sealing and CTE-matching in optical dome interfacing while maintaining optical precision/accuracy. Therefore, as will be appreciated, such designs typically have suffered from degraded optical performance and general system reliability complications.

Therefore, there is need for an optical dome interface which minimizes/eliminates CTE-mismatching complications while providing an environmental seal that sufficiently protects internally housed optics/electronics from external hazards over a wide range of temperatures and minimizing errors/deviations in optical precision/accuracy that result from removal/replacement of components of the interface.

Thus, and in accordance with an embodiment of the present invention, techniques are disclosed for implementing an optical dome bezel for interfacing an optical dome and a housing comprising materials of different CTEs, while providing an environmental seal which protects internally housed optics/electronics and maintaining optical performance of the system over a broad range of temperatures and operating conditions.

In some cases, embodiments of the present invention may be configured to be easily removable/interchangeable/replaceable while providing reproducible precision/accuracy in terms of the alignment of the optical dome relative to the internal optics and/or housing.

In some cases, embodiments of the present invention may realize reductions in cost while mitigating/eliminating difficulties typically resulting from use of a low-CTE optical dome material and a relatively higher-CTE housing material.

In some cases, embodiments of the present invention may provide, for example: (1) a bezel-to-dome interface that is substantially stress-free over a broad temperature range; and/or (2) a bezel-to-housing interface that is low-stress over a broad temperature range and exhibits radially compliant flexure.

Structure and Operation

FIG. 1 illustrates an exploded view of an optical dome bezel assembly 100 configured in accordance with an embodiment of the present invention. As can be seen, assembly 100 may include an optical dome bezel 110 configured to receive or otherwise operatively couple with an optical dome 150. In some embodiments, optical dome bezel 110 may include, for example, a mounting ring 120, an integral environmental sealing feature 130, and, optionally, a protective ring/sleeve 140. As will be appreciated in light of this disclosure, optical dome bezel 110 may include additional, fewer, and/or different elements or components from those here described, and the claimed invention is not intended to be limited to any particular bezel and/or optical system configuration, but instead can be used with numerous configurations in numerous applications.

Figure 2A:
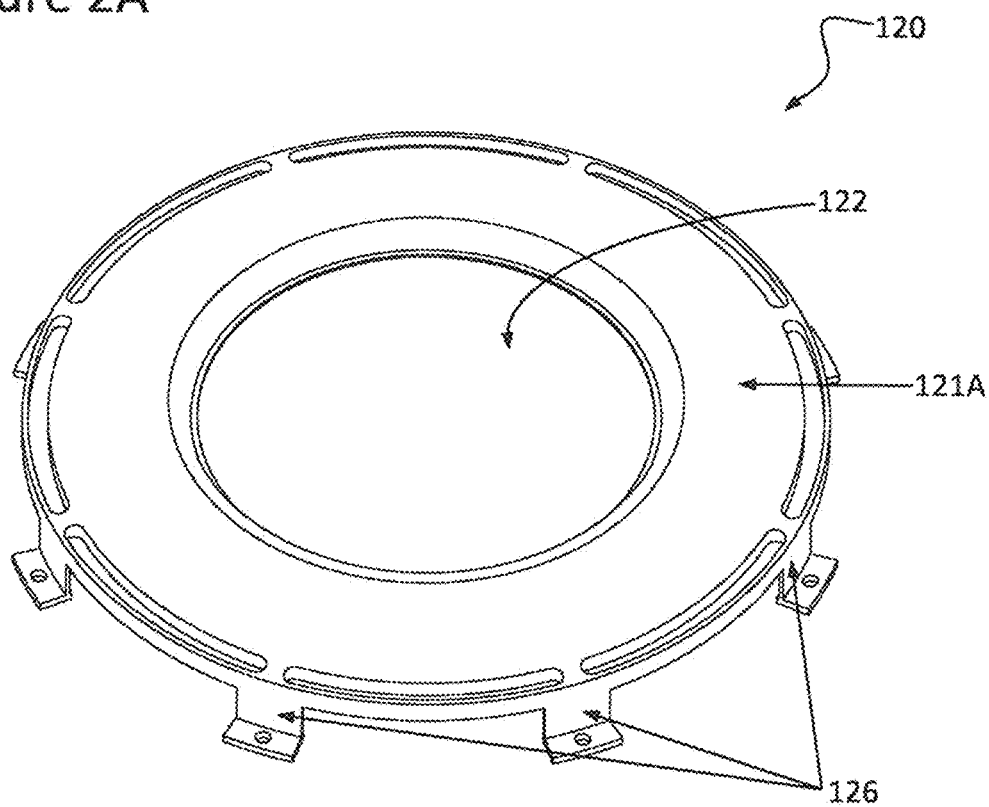
FIG. 2A illustrates a top perspective view of a mounting ring of an optical dome bezel configured in accordance with an embodiment of the present invention.
Figure 2B:
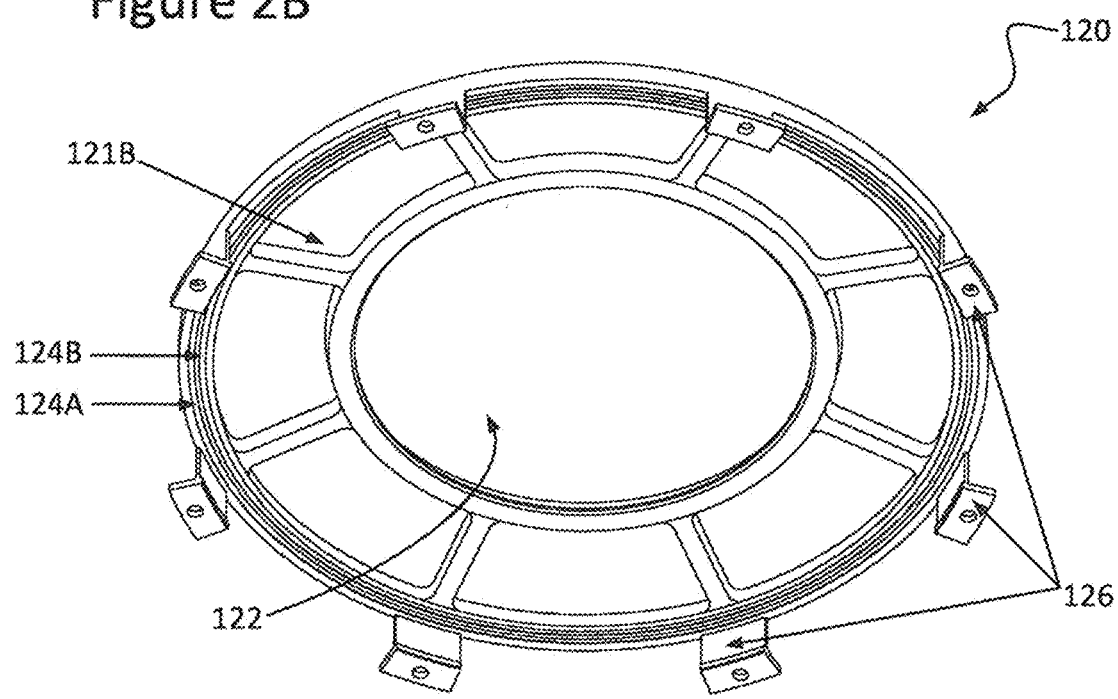
FIG. 2B illustrates a bottom perspective view of a mounting ring of an optical dome bezel configured in accordance with an embodiment of the present invention.

FIGS. 2A and 2B illustrate a top perspective and a bottom perspective view, respectively, of a mounting ring 120 of an optical dome bezel 110 configured in accordance with an embodiment of the present invention. As can be seen, and in accordance with a specific example embodiment, mounting ring 120 may be of a substantially circular (e.g., annular) shape. However, the claimed invention is not so limited, as mounting ring 120 may be of any given shape and/or dimensions suitable for a given application; for example, in some alternative embodiments, mounting ring 120 may be of a substantially non-circular shape (e.g., elliptical, rectangular, square, etc.) or other custom shape. Mounting ring 120 (and more generally, optical dome bezel 110) may be of sufficient dimensions, for example; (1) to permit it to be fitted onto/into a housing 160 or other suitable surface/locus, discussed in detail below with reference to FIGS. 3A and 3B; (2) to provide sufficient physical support for an optical dome 150; (3) to physically protect any optics/electronics housed therein; and/or (4) to permit the internal optics to gather information from a scene within the optical system's field of view (FOV). Other suitable geometries/configurations of mounting ring 120 will depend on a given application and will be apparent in light of this disclosure.

In accordance with an embodiment of the present invention, a number of factors may be considered in choosing a suitable, material to be implemented in mounting ring 120, including, but not limited to: (1) the compatibility of the material with heat treatment processes; (2) the strength and flexibility/resilience profile of the material; (3) the durability of the material (e.g., corrosion resistance); (4) the fabricability of the material; and/or (5) the CTE-compatibility of the material with tire optical dome 150 material (e.g., exact match or otherwise within an acceptable tolerance, such as a difference in the range of about 20% or better, 10% or better, or 5% or better). Thus, and in accordance with an embodiment, mounting ring 120 may comprise, for example: (1) Grade 5 titanium alloy (Ti-6Al-4V); (2) a low-expansion iron-nickel alloy; (3) a low-expansion stainless steel: and/or (4) an aluminum-beryllium composite (e.g., ALBEMET®). Other suitable materials for mounting ring 120 will depend on a given application and will be apparent in light of this disclosure.

As can further be seen from the example embodiment depicted by FIGS. 2A and 2B, mounting ring 120 may have an aperture 122 defined therein. In some cases, aperture 122 may be, for example, substantially centrally located in the body of mounting ring 120 and may pass through from an outer surface 121A to an inner surface 121B thereof. Aperture 122 may be of any given shape/dimensions (e.g., circular, elliptical, rectangular, square, etc.) and may be configured, at least in part, based on the general geometry of optical dome bezel 110 and/or the optics/electronics to be housed within optical dome bezel assembly 100. In some embodiments, aperture 122 may be configured to permit an optical dome 150 to be joined at that location. In some instances, multiple apertures (e.g., aperture 122 and at least one other aperture) may be formed in mounting ring 120, one or more of which may permit accommodation of optics/electronics componentry. Other suitable configurations of aperture 122 and/or other apertures/accommodations will depend on a given application and will be apparent in light of this disclosure.

As can further be seen from the example embodiment depicted in FIGS. 2A and 2B, mounting ring 120 may include a plurality of flexure blades 126 configured to permit radially compliant flexure. In some cases, embodiments implementing such a plurality of flexure blades 126 may reduce the vulnerability of optical dome bezel assembly 100 (and its internal optics/electronics) to physical stresses, such as those exerted by vibration and/or thermal expansion/contraction.

Flexure blades 126 may be positioned at various locations on mounting ring 120; for instance, in one specific, example embodiment, flexure blades 126 may be disposed along an outer perimeter of mounting ring 120. In some cases, flexure blades 126 may be configured to extend/project outwardly from (e.g., substantially perpendicular to), for example, inner surface 121B of mounting ring 120, In accordance with an embodiment, the spacing of the individual flexure blades 126 on mounting ring 120 may be at regular (e.g., equidistant) or irregular intervals and may be of uniform or varied shape, size, and/or orientation. Flexure blades 126 may be configured to permit mounting ring 120 (and thus optical dome bezel 110) to be secured or mated with a housing 160 or other surface/locus, discussed in detail below with reference to FIGS. 3A and 3B. The quantity (e.g., 2-12, or more), durability, and/or resilience of flexure blades 126 may be tailored, in accordance with an embodiment, to support and stabilize optical dome bezel 110 (and an attendant optical dome ISO) while in contact with a housing 160 or other surface/locus, while allowing sufficient flexibility in a radially compliant manner. Other suitable configurations for flexure blades 126 will depend on a given application and will be apparent in light of this disclosure.

Returning to FIG. 1, optical dome bezel 110 may include an integral environmental sealing feature 130 configured to protect the internal volume of assembly 100 from external environmental hazards, in accordance with an embodiment. For instance, as can be seen with reference to FIG. 2B, and in accordance with one specific example embodiment, mounting ring 120 may include one or more sealing channels 124A/124B running about/integral to mounting ring 120. In some cases, sealing channels 124A and/or 124B (and any additional sealing channels that optionally may be included) may be disposed/formed, for example, in the inner surface 121B of mounting ring 120. In the specific example embodiment depicted, mounting ring 120 includes an outer channel 124A and an inner channel 124B (e.g., located at a lesser radial distance than outer channel 124A, as measured from the center of mounting ring 120). As will be appreciated, while the specific example embodiment depicted in FIG. 2B shows two sealing channels 124A and 124B, other embodiments may have fewer (e.g., one) or more (e.g., three to five, or more) sealing channels formed in or otherwise integral to mounting ring 120 of optical dome bezel 110. As will be appreciated further, and in accordance with an embodiment, sealing channels 124A and/or 124B may be of any given shape (e.g., circular, elliptical, rectangular, square, etc.) and may be configured, at least in past, based on: (1) the shape/dimensions of mounting ring 120; (2) the general geometry of optical dome bezel 110; (3) the inclusion of aperture 122 and/or other optional apertures/accommodations; and/or (4) the optics/electronics to be housed within optical dome bezel assembly 100.

Sealing channels 124A and/or 124B may be configured to receive or otherwise retain, for example, a material suitable for forming integral environmental sealing 130 capable of protecting the internal optics/electronics from a variety of external environmental hazards, such as, but not limited to: water (e.g., rain, humidity, moisture, steam); corrosive fluids/vapors (e.g., fuels, lubricants/greases, brake fluids, solvents, ozone); particulates (e.g., dust, smoke): and/or debris. In accordance with an embodiment, integral environmental sealing feature 130 may be configured to operate, for example, in the range of about −60° C. to 90° C. (e.g., −54° C. to 71° C.). Other suitable resistances and/or operating temperatures will depend on a given application and will be apparent in light of this disclosure.

In some embodiments, sealing channel 124A may be configured to receive/retain, for example, an O-ring gasket 134A that is pressed into or otherwise deposited/formed therein, and an O-ring gasket 134B may be similarly implemented in corresponding sealing channel 124B. In accordance with an embodiment, a series of O-ring gaskets may be integrated into a corresponding number of sealing channels located/formed in mounting ring 120 (e.g., on its inner surface 121B).

Outer O-ring gasket 134A may comprise, for example, a robust material, which resists a variety of substances (e.g., fuels, lubricants, corrosive/degrading materials, etc.) that may be found in the external environment as well as which performs over a broad temperature range (e.g., −73° C. to 177° C.). Thus, and in accordance with one specific example embodiment, outer O-ring gasket 134A may comprise, for instance, fluorosilicone and may be configured to be disposed within outer sealing channel 124A.

Inner O-ring gasket 134B may comprise, for example, a low-permeability material which resists a variety of substances (e.g., rain/humidity/moisture, etc.) that may be found in the external environment, as well as which, performs over a broad temperature range (e.g., −59° C. to 121° C.). Thus, and in accordance with one specific example embodiment, inner O-ring gasket 134B may comprise, for instance, butyl and may be configured to be disposed within inner sealing channel 124B.

As will be appreciated, any number of suitable sealing materials may be used to provide integral environmental sealing 130, and the claimed invention is not intended to be limited to the aforementioned O-ring gaskets. For example, in an alternative embodiment, materials/compounds having suitable characteristics (e.g., similar to those of the aforementioned O-ring gaskets 134A and/or 134B) may be disposed or otherwise provided in situ within sealing channels 124A and/or 124B. Other suitable sealing materials/configurations will depend on a given application and will be apparent in light of this disclosure.

In accordance with an embodiment, O-ring gasket 134A and/or O-ring gasket 134B (or other sealing material/compound) may be configured to be brought into sealing engagement, for example, with a portion of housing 160 (e.g., an upper surface and/or outer perimeter thereof) and/or other suitable surface/locus so as to provide suitable protection of optics/electronics housed therein.

Returning to FIG. 1, optical dome 150 may be configured, in whole or in part, as any shape suitable for a given application, such as, but not limited to: (1) ellipsoidal (e.g., sphere, ellipsoid); (2) polyhedral (e.g., cube, prism, rectangular cuboid); (3) cylindrical (e.g., elliptic cylinder, circular cylinder); and/or (4) other suitable three-dimensional configuration. In one specific example embodiment, optical dome 150 may be a sphere configured to operatively couple with, for example, optical dome bezel 110 (e.g., at aperture 122). However, the claimed invention is not so limited; for example, in an alternative embodiment, optical dome 150 may be a planar or curvilinear/non-planar window configured to be operatively coupled with optical dome bezel 110. Other suitable geometries/dimensions for optical dome 150 will depend on a given application and will be apparent in light of this disclosure.

In accordance with an embodiment of the present invention, a number of factors may be considered in choosing a suitable material to be implemented in optical dome 150, including, but not limited to: (1) the wavelength range of interest to the internal optics/electronics (e.g., infrared, ultraviolet, visible, etc); (2) the CTE-compatibility of the material with mounting ring 120 and/or housing 160 (e.g., exact match or otherwise within an acceptable tolerance, such as a difference in the range of about 20% or better, 10% or better, or 5% or better); and/or (3) durability (e.g., impact resistance, abrasion/scratch resistance, corrosion resistance, etc.). Thus, and in accordance with an embodiment, optical dome 150 may be implemented, for instance, with a low-expansion optical material, such as, but not limited to: (1) aluminum oxynitride (ALON); (2) silicon (Si); (3) germanium (Ge); and/or (4)

sapphire ($Al_2O_3$). Other suitable materials for optical dome 150 will depend on a given application and will be apparent in light of this disclosure.

Figure 3A:
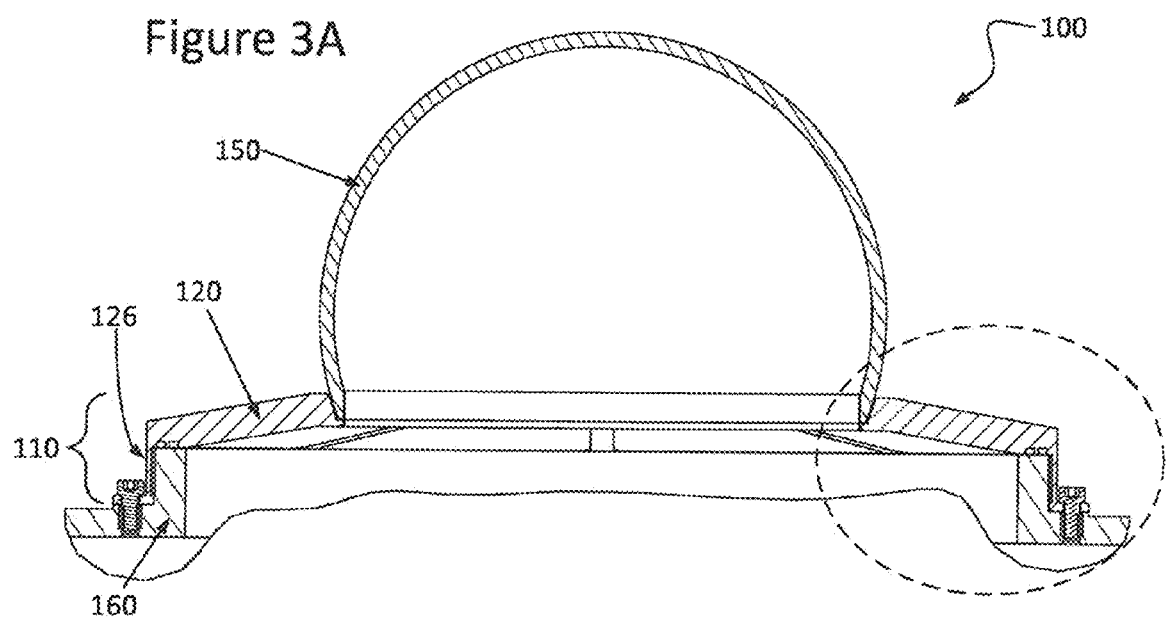
FIG. 3A illustrates a cross-section view of an optical dome bezel assembly configured in accordance with an embodiment of the present invention.
Figure 3B:
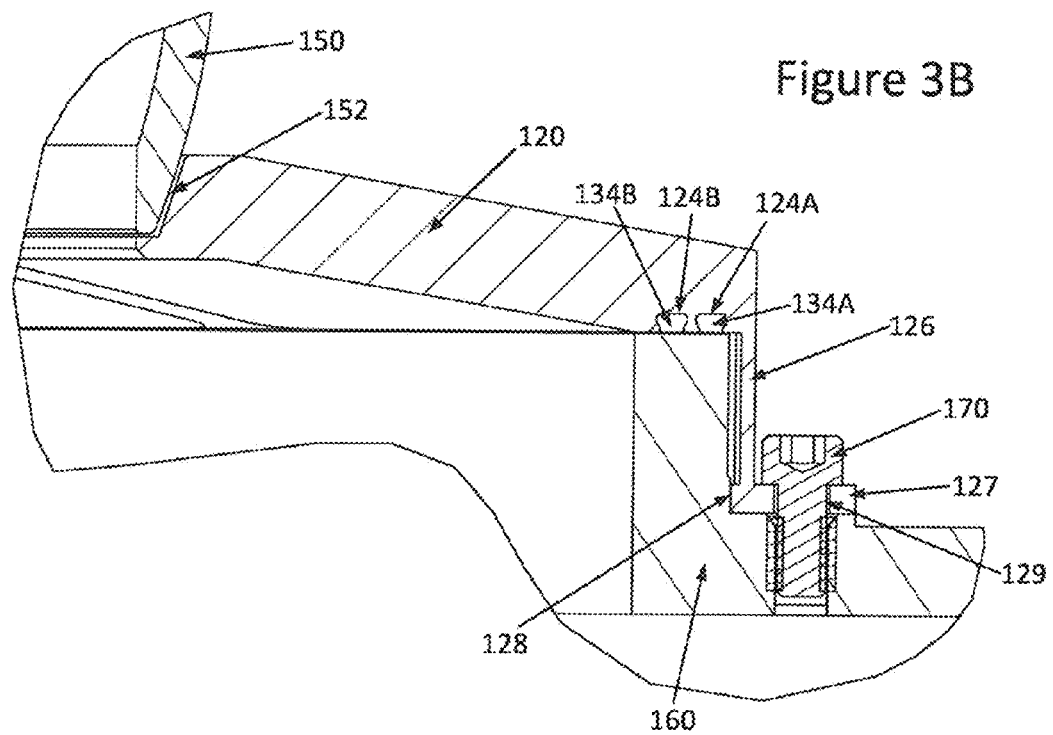
FIG. 3B illustrates a partial, cross-section view of the optical dome bezel assembly of FIG. 3A, the view corresponding to the portion enclosed by the dashed ellipse therein.

FIG. 3A illustrates a cross-section view of an optical dome bezel assembly 100 configured in accordance with an embodiment of the present invention. FIG. 3B illustrates a partial, cross-section view of the optical dome bezel assembly 100 of FIG. 3A, the view corresponding to the portion enclosed by the dashed ellipse therein.

As previously discussed, and in accordance with an embodiment, mounting ring 120 of optical dome bezel 110 may include a radially compliant flexure feature such as a plurality of flexure blades 126 located, for example, along an outer perimeter of mounting ring 120 and extending/projecting outwardly from (e.g., substantially perpendicular to), for example, an inner surface 121B of mounting ring 120. Flexure blades 126 may be configured, in accordance with an embodiment, to engage a housing 160 or other suitable surface/locus. Housing 160 may comprise or otherwise include, for example, a portion of a building or other physical structure, a piece of equipment, or a vehicle (e.g., in/on the fuselage of an aircraft; in/on an automobile). As will be appreciated in light of this disclosure, numerous mountable platforms, surfaces, and/or locations may comprise housing 160, and the claimed invention is not intended to be limited to any particular type/configuration thereof.

As can be seen in the example embodiment depicted in FIG. 3B, a given flexure blade 126 may include a flexure foot 12 configured to be mounted/coupled to a housing 160, thereby securing optical dome bezel 110 (and attendant optical dome 150) to housing 160. Flexure foot 127 may have disposed therein a fastening aperture 129 configured to receive, for example, a fastener 170 to help mount/secure optical dome bezel 110 to housing 160.

As can further be seen in the example embodiment depicted in FIG. 3B, a given flexure foot 127 may include a precision alignment feature 128 (e.g., a piloting diameter) configured to permit precision alignment of optical dome bezel 110 (and consequently attendant optical dome 150) with housing 160 on which it is mounted/secured. Precision alignment feature 128 may be configured to allow optical dome bezel 110 to maintain accuracy/precision in terms of the location of the optical dome 150 relative to the housing 160 and/or the internal optics/electronics while also providing efficient, repeatable removal/replacement of optical dome bezel 110. Precision alignment feature 128 may comprise, for example, a small, heel-like inset/protrusion located on an interior side of a given flexure foot 127 and may be configured, for example, to snugly contact/engage housing 160 with repeatable/efficient consistency. Other suitable precision alignment features/configurations will depend on a given application and will be apparent in light of this disclosure.

Figure 4:
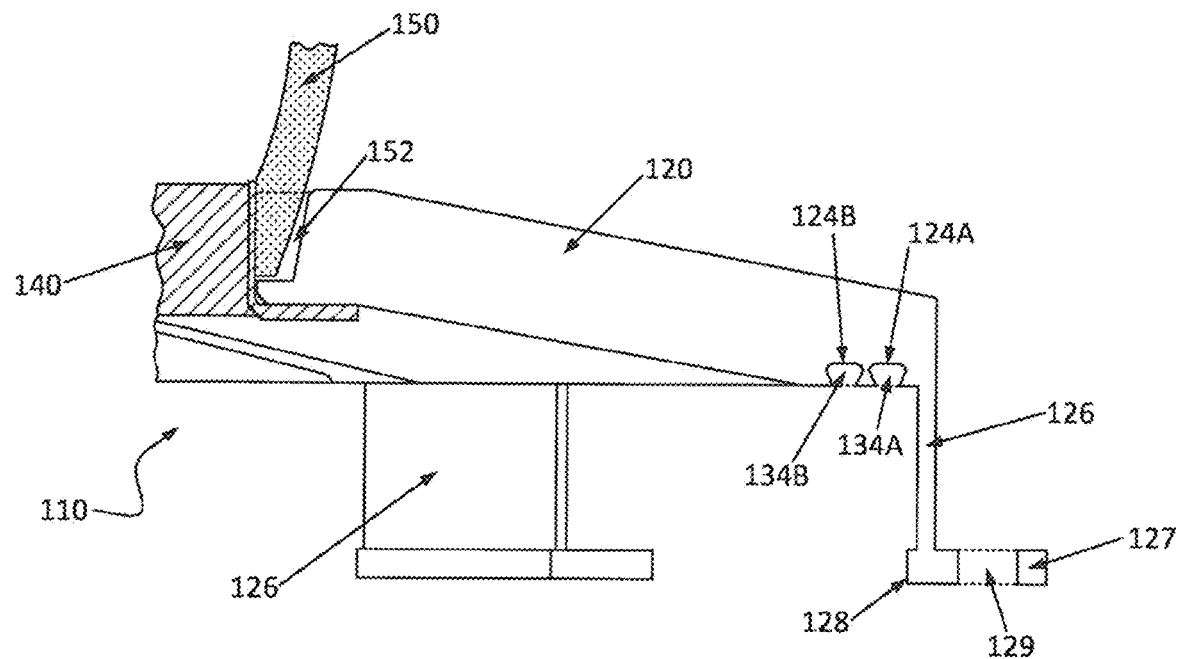
FIG. 4 illustrates a partial, cross-section view of an optical dome bezel assembly implementing an optional protective ring/sleeve in accordance with an embodiment of the present invention.

As can be seen from FIG. 3B and FIG. 4, for example, and in accordance with an embodiment of the present invention, one or more portions of mounting ring 120 (e.g., aperture 122) of optical dome bezel 110 may be configured to receive a quantity of adhesive sealant 152. In some embodiments, adhesive sealant 152 may help to secure optical dome 150 to optical dome bezel 110, while maintaining the desired environmental seal. Adhesive sealant 152 may comprise, for example, a flexible and/or low-outgassing adhesive sealant material which performs over a broad temperature range (e.g., −135° C. to 300° C., or higher). Thus, and in accordance with one specific example embodiment, adhesive sealant 152 may comprise, for instance, RTV566 silicone and may be capable of being disposed within at least a portion of aperture 122. However, the claimed invention is not so limited; for example, and in accordance with an alternative embodiment, adhesive sealant 152 may comprise an epoxy adhesive (e.g., SCOTCH-WELD™ Epoxy Adhesive 2216) with suitable physical properties (e.g., sufficient rigidity, flexibility, impermeability, resistances, etc.) and/or thermal properties (e.g., CTE matching). Other suitable adhesive sealants 152 will depend on a given application and will be apparent in light of this disclosure.

FIG. 4 illustrates a partial, cross-section view of an optical dome bezel assembly 100 implementing an optional protective ring/sleeve 140 in accordance with an embodiment of the present invention. As can be seen, and in accordance with an embodiment, an optional protective ring/sleeve 140 may be implemented within aperture 122 and configured, for example, so as to line/cover at least a portion of the interior (e.g., inner wall) of aperture 122 and thus protect against, for example, damage to mounting ring 120 and/or damage to optical dome 150 (e.g., chipping/cracking) during mounting (e.g., installation, removal, etc.) of optical dome bezel assembly 100 with housing 160. As will be appreciated, and in accordance with an embodiment, optional protective ring/sleeve 140 may be configured to be permanently and/or temporarily installed in aperture 122 (e.g., configured to be removable from optical dome bezel 110).

In accordance with an embodiment of the present invention, a number of factors may be considered in choosing a suitable material to be implemented in optional protective ring/sleeve 140, including, but not limited to: (1) the compatibility of the material with heat treatment processes; (2) the strength and flexibility/resilience profile of the material; (3) the durability of the material (e.g., corrosion resistance); (4) the fabricability of the material; and/or (5) the CTE-compatibility of the material with the optical dome 150 material and/or mounting ring 120 material (e.g., exact match or otherwise within an acceptable tolerance, such as a difference in the range of about 20% or better, 10% or better, or 5% or better). Thus, and in accordance with an embodiment, optional protective ring/sleeve 140 may comprise, for example: (1) Grade 5 titanium alloy (Ti-6Al-4V); (2) a low-expansion iron-nickel alloy; (3) a low-expansion stainless steel; and/or (4) an aluminum-beryllium composite (e.g., ALBEMET®). In some cases, the material implemented in optional protective ring/sleeve 140 may be chosen, at least in part, based on the material implemented in mounting ring 120 (e.g., if mounting ring 120 comprises Ti-6Al-4V, then optional protective ring/sleeve 140 also may comprise Ti-6Al-4V, so as to maintain CTE matching). Other suitable materials/configurations for optional protective ring/sleeve 140 will depend on a given application and will be apparent in light of this disclosure.

Figure 5A:
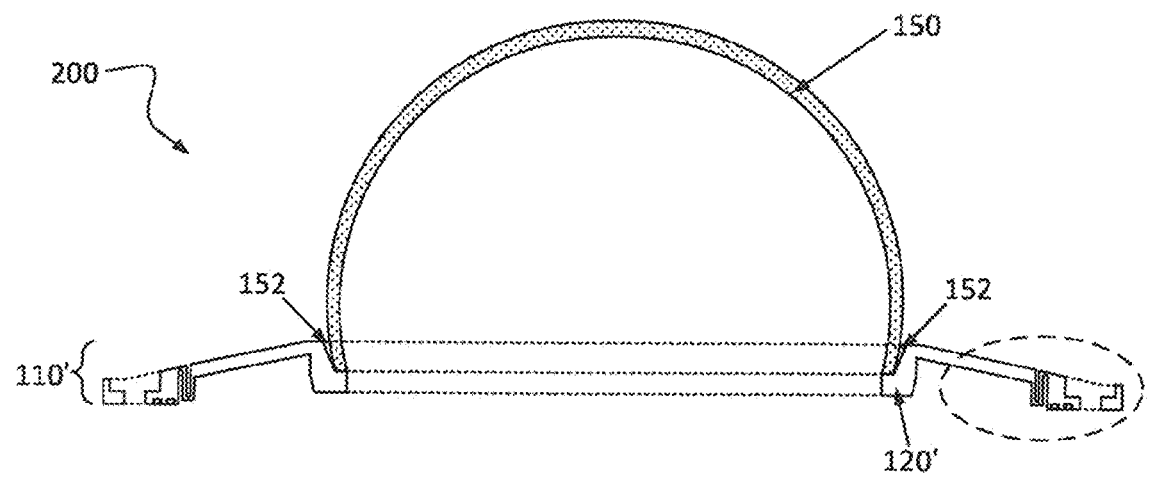
FIG. 5A illustrates a cross-section view of an optical dome bezel assembly configured in accordance with an embodiment of the present invention.

FIG. 5A illustrates a cross-section view of an optical dome bezel assembly 200 configured in accordance with an embodiment of the present invention. FIG. 5B illustrates a partial, cross-section view of the optical dome bezel assembly of FIG. 5A, the view corresponding to the portion enclosed by the dashed ellipse therein.

As will be apparent in light of this disclosure, and in accordance with an embodiment, mounting ring 120' is an alternative configuration of mounting ring 120, discussed in detail above. As can be seen, mounting ring 120' may be configured, in some embodiments, to include a continuous spring-form S-channel 226 integrally formed therein, which permits radially compliant flexure and/or reduces the vulnerability of an optical dome bezel assembly 200 (and its internal optics/electronics) to physical stresses such as those exerted by vibration and/or thermal expansion/contraction. In some cases, spring-form S-channel 226 may be integrated into mounting ring 120' along a circumference of lesser radial distance than, for example, inner sealing channel 124B so as to preserve environmental sealing.

FIG. 6A illustrates a partial, cross-section view of an optical dome bezel assembly 200 configured in accordance with an embodiment of the present invention. FIG. 6B illustrates a partial, cross-section view of the optical dome bezel assembly of FIG. 6A, the view corresponding to the portion enclosed by the dashed ellipse therein.

As can be seen, in accordance with one specific example embodiment, mounting-ring 120' need not be of uniform/homogeneous thickness and/or other dimension when an integral spring-form S-channel 226 is implemented therein. For example, a distal portion 120a of mounting ring 120' may be of greater thickness (and/or other dimension) than a proximal portion 120b of mounting ring 120'. In some such instances, this may help integral spring-form S-channel 226 to provide sufficient radially compliant flexure and/or reduce the vulnerability of an optical dome bezel assembly 200 (and its internal optics/electronics) to physical stresses such as those exerted by vibration and/or thermal expansion/contraction. While the specific example embodiment illustrated in FIG. 5A-5B and FIG. 6A-6B depicts a single spring-form S-channel 226 configured to run continuously about a circumference of mounting ring 120' of optical dome bezel 110', the claimed invention is not so limited; for example, in an alternative embodiment, multiple continuous spring-form S-channels 226 may be integrated at various locations/radial distances in mounting ring 120', including portions closer to the center of mounting ring 120'. Other suitable configurations/locations for spring-form S-channel 226 will depend on a given application and will be apparent in light of this disclosure.

The foregoing description of the embodiments of the invention has been presented for the purposes of illustration and description. It is not intended to be exhaustive or to limit the invention to tire precise form disclosed. Many modifications and variations are possible in light of this disclosure. It is intended that the scope of the invention be limited not by this detailed description, but rather by the claims appended hereto.

What is claimed is:

1. An apparatus comprising:
   a mounting ring having an aperture passing therethrough from an exterior surface of the mounting ring to an opposing, interior surface thereof;
   a radially compliant flexure feature integral with the mounting ring such that the mounting ring and the radially compliant flexure feature constitute a monolithic piece; and
   an environmental sealing feature integral with the mounting ring.

2. The apparatus of claim 1, wherein the mounting ring comprises at least one of Grade 5 titanium alloy (Ti-6Al-4V), a low-expansion iron-nickel alloy, a low-expansion stainless steel, and an aluminum-beryllium composite.

3. The apparatus of claim 1, wherein the aperture is configured to receive a quantity of adhesive sealant for bonding an optical dome/window to the mounting ring.

4. The apparatus of claim 1, wherein the radially compliant flexure feature comprises a plurality of flexure blades disposed along an outer perimeter of the mounting ring and extending substantially perpendicular to the interior surface of the mounting ring.

5. The apparatus of claim 4, wherein at least one flexure blade further comprises:
   a flexure foot located at a distal end of the flexure blade and extending radially outward substantially parallel to the interior surface of the mounting ring; and
   a precision alignment feature located at the distal end of the flexure blade, positioned opposite the flexure foot, and extending radially inward substantially parallel to the interior surface of the mounting ring.

6. The apparatus of claim 1, wherein the radially compliant flexure feature comprises a continuous spring-form S-channel integrally formed in the mounting ring.

7. The apparatus of claim 1, wherein the environmental sealing feature comprises:
   a first channel integral with the interior surface of the mounting ring at a first radial distance; and
   a second channel integral with the interior surface of the mounting ring at a second radial distance of lesser radius than the first channel.

8. The apparatus of claim 7, wherein at least one of the first channel and the second channel contains a sealing material that is resistant to at least one of water, rain, humidity, moisture, steam, corrosive fluids, corrosive vapors, fuels, lubricants, greases, solvents, ozone, particulates, dust, smoke, and debris over a temperature range of about −60° C. to 90° C.

9. The apparatus of claim 7, wherein the first channel contains a fluorosilicone O-ring gasket, and the second channel contains a butyl O-ring gasket.

10. The apparatus of any of claims 1-9 further comprising a protective ring/sleeve configured to be received by the aperture and to protect at least one of at least a portion of the mounting ring and an optical dome/window received by the mounting ring during operative coupling of the apparatus with a housing.

11. The apparatus of claim 10, wherein the protective ring/sleeve comprises the same material as the mounting ring.

12. A system comprising:
   an optical dome/window; and
   a bezel configured to receive the optical dome/window, wherein the bezel comprises:
      a mounting ring having an aperture passing therethrough from an exterior surface of the mounting ring to an opposing, interior surface thereof;
      a radially compliant flexure feature integral with the mounting ring such that the mounting ring and the radially compliant flexure feature constitute a monolithic piece; and
      an environmental sealing feature integral with the mounting ring.

13. The system of claim 12, wherein the optical dome/window comprises at least one of aluminum oxynitride (ALON), silicon, germanium, and sapphire.

14. The system of claim 12, wherein the optical dome/window is configured with a geometry selected from the group consisting of spherical, ellipsoidal, polyhedral, cubic, prismatic, cylindrical, planar, curvilinear, and non-planar.

15. The system of claim 12, wherein the mounting ring comprises at least one of Grade 5 titanium alloy (Ti-6Al-4V), a low-expansion iron-nickel alloy, a low-expansion stainless steel, and an aluminum-beryllium composite.

16. The system of claim 12, wherein the radially compliant flexure feature comprises a plurality of flexure blades positioned along an outer perimeter of the mounting ring and extending substantially perpendicular to the interior surface of the mounting ring.

17. The system of claim 16, wherein at least one flexure blade further comprises:

a flexure foot located at a distal end of the flexure blade and extending radially outward substantially parallel to the interior surface of the mounting ring; and a precision alignment feature located at the distal end of the flexure blade, positioned opposite the flexure foot, and extending radially inward substantially parallel to the interior surface of the mounting ring.

18. The system of claim 12, wherein the radially compliant flexure feature comprises a continuous spring-form S-channel integrally formed in the mounting ring.

19. The system of claim 12, wherein the environmental sealing feature comprises:
   a first channel integral with the interior surface of the mounting ring at a first radial distance; and
   a second channel integral with the interior surface of the mounting ring at a second radial distance of lesser radius than the first channel;
   wherein at least one of the first channel and the second channel contains an O-ring gasket that is resistant to at least one of water, rain, humidity, moisture, steam, corrosive fluids, corrosive vapors, fuels, lubricants, greases, solvents, ozone, particulates, dust, smoke, and debris over a temperature range of about $-60°$ C. to $90°$ C.

20. The system of any of claims 12-19, wherein the bezel further comprises a protective ring/sleeve configured to be received by the aperture and to protect at least one of at least a portion of the mounting ring and optical dome/window during operative coupling of the bezel with a housing.

21. The system of any of claims 12-19, wherein the bezel is configured to operatively couple with a housing comprising a material having a different coefficient of thermal expansion from that of the optical dome/window, and wherein the bezel is configured to at least one of provide a substantially stress-free bezel-to-optical dome/window interface over a temperature range of about $-60°$ C. to $90°$ C. and provide a low-stress bezel-to-housing interface over a temperature range of about $-60°$ C. to $90°$ C. while exhibiting radially compliant flexure.

22. A system comprising:
   a bezel comprising:
      an annular mounting ring having an aperture passing therethrough from an exterior surface of the mounting ring to an opposing, interior surface thereof;
      a plurality of flexure blades positioned along an outer perimeter of the mounting ring, wherein the flexure blades extend substantially perpendicular to the inner surface of the mounting ring, and wherein at least one flexure blade further comprises:
         a flexure foot located at a distal end of the flexure blade and extending radially outward substantially parallel to the interior surface of the mounting ring; and
         a precision alignment feature located at the distal end of the flexure blade, positioned opposite the flexure foot, and extending radially inward substantially parallel to the interior surface of the mounting ring;
      a first channel formed in the interior surface of the mounting ring at a first radial distance;
      a fluorosilicone O-ring gasket disposed within the first channel;
      a second channel formed in the interior surface of the mounting ring at a second radial distance of lesser radius than the first channel; and
      a butyl O-ring gasket disposed within the second channel; and
   an optical dome/window operatively coupled to the bezel at the aperture.

23. The system of claim 22, wherein the mounting ring comprises a material having a coefficient of thermal expansion within 20% or less than that of the optical dome/window.

24. The system of claim 22, wherein the bezel further comprises a protective ring/sleeve configured to be received by the aperture and to protect at least one of at least a portion of the bezel and optical dome/window during operative coupling of the bezel with a housing, and wherein the protective ring/sleeve comprises a material having a coefficient of thermal expansion within 20% or less than that of at least one of the mounting ring and the optical dome/window.

25. The system of any of claims 22-24, wherein the bezel is configured to operatively couple with a housing comprising a material having a different coefficient of thermal expansion from that of the optical dome/window, and wherein the bezel is configured to at least one of provide a substantially stress-free bezel-to-optical dome/window interface over a temperature range of about $-60°$ C. to $90°$ C. and provide a low-stress bezel-to-housing interface over a temperature range of about $-60°$ C. to $90°$ C. while exhibiting radially compliant flexure.

\* \* \* \* \*